(12) United States Patent
Lamego et al.

(10) Patent No.: US 7,957,780 B2
(45) Date of Patent: Jun. 7, 2011

(54) PHYSIOLOGICAL PARAMETER CONFIDENCE MEASURE

(75) Inventors: Marcelo Lamego, Rancho Santa Margarita, CA (US); Mohamed Diab, Mission Viejo, CA (US); Ammar Al-Ali, Tustin, CA (US)

(73) Assignee: MASIMO Laboratories, Inc., Irvine, CA (US)

( * ) Notice: Subject to any disclaimer, the term of this patent is extended or adjusted under 35 U.S.C. 154(b) by 1498 days.

(21) Appl. No.: 11/367,034

(22) Filed: Mar. 1, 2006

(65) Prior Publication Data

US 2006/0211925 A1    Sep. 21, 2006

Related U.S. Application Data

(60) Provisional application No. 60/657,596, filed on Mar. 1, 2005, provisional application No. 60/657,281, filed on Mar. 1, 2005, provisional application No. 60/657,268, filed on Mar. 1, 2005, provisional application No. 60/657,759, filed on Mar. 1, 2005.

(51) Int. Cl.
*A61B 5/1455* (2006.01)
(52) U.S. Cl. .................................. 600/322; 600/310
(58) Field of Classification Search .............. 600/310, 600/322, 323, 336
See application file for complete search history.

(56) References Cited

U.S. PATENT DOCUMENTS

| | | | |
|---|---|---|---|
| 3,998,550 A | 12/1976 | Konishi et al. | |
| 4,157,708 A | 6/1979 | Imura | |
| 4,167,331 A | 9/1979 | Nielsen | |
| 4,266,554 A | 5/1981 | Hamaguri | |
| 4,446,871 A | 5/1984 | Imura | |
| 4,586,513 A | 5/1986 | Hamaguri | |
| 4,621,643 A | 11/1986 | New et al. | |
| 4,653,498 A | 3/1987 | New et al. | |
| 4,685,464 A | 8/1987 | Goldberger | |
| 4,694,833 A | 9/1987 | Hamaguri | |
| 4,700,708 A | 10/1987 | New et al. | |
| 4,714,341 A | 12/1987 | Hamaguri et al. | |
| 4,770,179 A | 9/1988 | New et al. | |
| 4,773,422 A | 9/1988 | Isaacson et al. | |
| 4,781,195 A | 11/1988 | Martin | |
| 4,800,885 A | 1/1989 | Johnson | |
| 4,832,484 A | 5/1989 | Aoyagi et al. | |
| 4,846,183 A | 7/1989 | Martin | |
| 4,863,265 A | 9/1989 | Flower et al. | |
| 4,867,571 A | 9/1989 | Frick et al. | |

(Continued)

FOREIGN PATENT DOCUMENTS

WO    WO 98/43071    10/1998

(Continued)

OTHER PUBLICATIONS

International Search Report for PCT/US2006/007516, mailed on Jan. 11, 2007, in 4 pages.

(Continued)

*Primary Examiner* — Eric F Winakur
(74) *Attorney, Agent, or Firm* — Knobbe Marten Olson & Bear LLP

(57) ABSTRACT

Confidence in a physiological parameter is measured from physiological data responsive to the intensity of multiple wavelengths of optical radiation after tissue attenuation. The physiological parameter is estimated based upon the physiological data. Reference data clusters are stored according to known values of the physiological parameter. At least one of the data clusters is selected according to the estimated physiological parameter. The confidence measure is determined from a comparison of the selected data clusters and the physiological data.

9 Claims, 6 Drawing Sheets

U.S. PATENT DOCUMENTS

| | | | |
|---|---|---|---|
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| RE33,643 E | 7/1991 | Isaacson et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,078,136 A | 1/1992 | Stone et al. |
| 5,163,438 A | 11/1992 | Gordon et al. |
| 5,190,040 A | 3/1993 | Aoyagi |
| 5,209,230 A | 5/1993 | Swedlow et al. |
| 5,259,381 A | 11/1993 | Cheung et al. |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,331,549 A | 7/1994 | Crawford, Jr. |
| 5,335,659 A | 8/1994 | Pologe et al. |
| 5,337,744 A | 8/1994 | Branigan |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| 5,421,329 A | 6/1995 | Casciani et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| RE35,122 E | 12/1995 | Corenman et al. |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,551,423 A | 9/1996 | Sugiura |
| 5,553,615 A | 9/1996 | Carim et al. |
| 5,555,882 A | 9/1996 | Richardson et al. |
| 5,562,002 A | 10/1996 | Lalin |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,713,355 A | 2/1998 | Richardson et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,348 A | 9/1998 | Kaestle et al. |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley |
| 5,830,131 A | 11/1998 | Caro et al. |
| 5,830,137 A | 11/1998 | Sharf |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,851,178 A | 12/1998 | Aronow |
| 5,851,179 A | 12/1998 | Ritson et al. |
| 5,853,364 A | 12/1998 | Baker, Jr. et al. |
| 5,857,462 A | 1/1999 | Thomas et al. |
| 5,860,919 A | 1/1999 | Kiani-Azarbayjany et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,024 A | 4/1999 | Jarman et al. |
| 5,904,654 A | 5/1999 | Wohltmann et al. |
| 5,910,108 A | 6/1999 | Solenberger |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling |
| 5,978,691 A | 11/1999 | Mills |

| Patent No. | Date | Inventor |
|---|---|---|
| 5,983,122 A | 11/1999 | Jarman et al. |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,023,541 A | 2/2000 | Merchant et al. |
| 6,027,452 A | 2/2000 | Flaherty et al. |
| 6,036,642 A | 3/2000 | Diab et al. |
| 6,045,509 A | 4/2000 | Caro et al. |
| 6,064,898 A | 5/2000 | Aldrich |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,110,522 A | 8/2000 | Lepper, Jr. et al. |
| 6,112,107 A | 8/2000 | Hannula |
| 6,122,042 A | 9/2000 | Wunderman et al. |
| 6,144,868 A | 11/2000 | Parker |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,236,872 B1 | 5/2001 | Diab et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,304,675 B1 | 10/2001 | Osbourn et al. |
| 6,304,767 B1 | 10/2001 | Soller et al. |
| 6,321,100 B1 | 11/2001 | Parker |
| 6,330,468 B1 | 12/2001 | Scharf |
| 6,334,065 B1 | 12/2001 | Al-Ali et al. |
| 6,341,257 B1 | 1/2002 | Haaland |
| 6,343,224 B1 | 1/2002 | Parker |
| 6,349,228 B1 | 2/2002 | Kiani et al. |
| 6,351,658 B1 | 2/2002 | Middleman et al. |
| 6,356,774 B1 | 3/2002 | Bernstein et al. |
| 6,360,114 B1 | 3/2002 | Diab et al. |
| 6,363,269 B1 | 3/2002 | Hanna et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,408,198 B1 | 6/2002 | Hanna et al. |
| 6,411,833 B1 | 6/2002 | Baker, Jr. et al. |
| 6,415,166 B1 | 7/2002 | Van Hoy et al. |
| 6,415,233 B1 | 7/2002 | Haaland |
| 6,415,236 B2 | 7/2002 | Kobayashi et al. |
| 6,430,525 B1 | 8/2002 | Weber et al. |
| 6,434,408 B1 | 8/2002 | Heckel |
| 6,441,388 B1 | 8/2002 | Thomas et al. |
| 6,453,184 B1 | 9/2002 | Hyogo et al. |
| 6,463,310 B1 | 10/2002 | Swedlow et al. |
| 6,463,311 B1 | 10/2002 | Diab |
| 6,470,199 B1 | 10/2002 | Kopotic et al. |
| 6,480,729 B2 | 11/2002 | Stone |
| 6,490,466 B1 | 12/2002 | Fein et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,528,809 B1 | 3/2003 | Thomas et al. |
| 6,537,225 B1 | 3/2003 | Mills |
| 6,541,756 B2 | 4/2003 | Schulz et al. |
| 6,542,764 B1 | 4/2003 | Al-Ali et al. |
| 6,546,267 B1 | 4/2003 | Sugiura |
| 6,553,241 B2 | 4/2003 | Mannheimer et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,031 B1 | 1/2004 | Porges et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |

| Patent No. | Date | Inventor |
|---|---|---|
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,993,371 B2 | 1/2006 | Kiani et al. |
| 6,996,427 B2 | 2/2006 | Ali et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 2001/0044700 A1 | 11/2001 | Koboyashi et al. |
| 2001/0045532 A1 | 11/2001 | Schulz et al. |
| 2002/0021269 A1 | 2/2002 | Rast |
| 2002/0038078 A1 | 3/2002 | Ito |
| 2002/0038081 A1 | 3/2002 | Fein et al. |
| 2002/0059047 A1 | 5/2002 | Haaland |
| 2002/0111748 A1 | 8/2002 | Kobayashi et al. |
| 2002/0156353 A1 | 10/2002 | Larson |
| 2002/0161291 A1 | 10/2002 | Kiani et al. |
| 2002/0183819 A1 | 12/2002 | Struble |
| 2003/0109775 A1 | 6/2003 | O'Neil et al. |
| 2003/0120160 A1 | 6/2003 | Yarita |
| 2003/0139657 A1 | 7/2003 | Solenberger |
| 2003/0195402 A1 | 10/2003 | Fein et al. |
| 2004/0006261 A1 | 1/2004 | Swedlow et al. |
| 2004/0033618 A1 | 2/2004 | Haass et al. |
| 2004/0034898 A1 | 2/2004 | Al Ali et al. |
| 2004/0059209 A1 | 3/2004 | Al Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0147823 A1 | 7/2004 | Kiani et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167382 A1 | 8/2004 | Gardner et al. |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0011488 A1 | 2/2005 | Al Ali et al. |
| 2005/0043902 A1 | 2/2005 | Haaland et al. |
| 2005/0049469 A1 | 3/2005 | Aoyagi et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0228253 A1 | 10/2005 | Debreczeny |
| 2005/0250997 A1 | 11/2005 | Takedo et al. |
| 2006/0030764 A1 | 2/2006 | Porges et al. |

FOREIGN PATENT DOCUMENTS

| | | |
|---|---|---|
| WO | WO 00/59374 | 10/2000 |
| WO | WO 03/068060 | 8/2003 |

OTHER PUBLICATIONS

Schmitt, Joseph M.; Zhou, Guan-Xiong; Miller, Justin, *Measurement of Blood Hematocrit by Dual-wavelength Near-IR Photoplethysmography*, published May 1992, Proc. SPIE vol. 1641, p. 150-161, Physiological Monitoring and Early Detection Diagnostic Methods, Thomas S. Mang; Ed. (SPIE homepage), in 12 pages.

Patent Cooperation Treaty (PCT) International Search Report; PCT/US 2006/007389; Date of Mailing Jul. 17, 2006; pp. 1-9.

PCT International Search Report; PCT/US2006/007537; Date of Mailing Jul. 17, 2006; pp. 1-10.

PCT International Search Report; PCT/US2006/007388; Date of Mailing Jul. 17, 2006; pp. 1-9.

PCT International Search Report; PCT/US2006/007538; Date of Mailing Jul. 17, 2006; pp. 1-9.

PCT International Search Report; PCT/US2006/007958; Date of Mailing Jul. 17, 2006; pp. 1-8.

PCT International Search Report; PCT/US2006/007506; Date of Mailing Jul. 17, 2006; pp. 1-10.

PCT International Search Report; PCT/US2006/007536; Date of Mailing Jul. 17, 2006; pp. 1-9.

PCT International Search Report; PCT/US2006/007540; Date of Mailing Jul. 17, 2006; pp. 1-9.

PCT International Search Report; PCT/US2006/007539; Date of Mailing Jul. 17, 2006; pp. 1-9.

PCT International Search Report; PCT/US2006/007387; Date of Mailing Jul. 17, 2006; pp. 1-9.

PHYSIOLOGICAL PARAMETER CONFIDENCE MEASURE

PRIORITY CLAIM TO RELATED PROVISIONAL APPLICATIONS

The present application claims priority benefit under 35 U.S.C. §119(e) to U.S. Provisional Patent Application Ser. No. 60/657,596, filed Mar. 1, 2005, entitled "Multiple Wavelength Sensor," No. 60/657,281, filed Mar. 1, 2005, entitled "Physiological Parameter Confidence Measure," No. 60/657,268, filed Mar. 1, 2005, entitled "Configurable Physiological Measurement System," and No. 60/657,759, filed Mar. 1, 2005, entitled "Noninvasive Multi-Parameter Patient Monitor." The present application incorporates the foregoing disclosures herein by reference.

CORPORATION BY REFERENCE OF COPENDING RELATED APPLICATIONS

| | application Ser. No. | Filing Date | Title |
|---|---|---|---|
| 1 | 11/367,013 | Mar. 1, 2006 | Multiple Wavelength Sensor Emitters |
| 2 | 11/366,995 | Mar. 1, 2006 | Multiple Wavelength Sensor Equalization |
| 3 | 11/366,209 | Mar. 1, 2006 | Multiple Wavelength Sensor Substrate |
| 4 | 11/366,210 | Mar. 1, 2006 | Multiple Wavelength Sensor Interconnect |
| 5 | 11/366,833 | Mar. 1, 2006 | Multiple Wavelength Sensor Attachment |
| 6 | 11/366,997 | Mar. 1, 2006 | Multiple Wavelength Sensor Drivers |
| 7 | 11/367,036 | Mar. 1, 2006 | Configurable Physiological Measurement System |
| 8 | 11/367,033 | Mar. 1, 2006 | Noninvasive Multi-Parameter Patient Monitor |
| 9 | 11/367,014 | Mar. 1, 2006 | Noninvasive Multi-Parameter Patient Monitor |
| 10 | 11/366,208 | Mar. 1, 2006 | Noninvasive Multi-Parameter Patient Monitor |

The present application incorporates the foregoing disclosures herein by reference.

BACKGROUND OF THE INVENTION

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \epsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

FIG. 1 illustrates $HbO_2$ and $Hb$ absorption $\mu_a$ versus wavelength. At red and near IR wavelengths below 970 nm, where water has a significant peak, $Hb$ and $HbO_2$ are the only significant absorbers normally present in the blood. Thus, typically only two wavelengths are needed to resolve the concentrations of $Hb$ and $HbO_2$, e.g. a red (RD) wavelength at 660 nm and an infrared (IR) wavelength at 940 nm. In particular, $SpO_2$ is computed based upon a red ratio $Red_{AC}/Red_{DC}$ and an IR ratio $IR_{AC}/IR_{DC}$, which are the AC detector response magnitude at a particular wavelength normalized by the DC detector response at that wavelength. The normalization by the DC detector response reduces measurement sensitivity to variations in tissue thickness, emitter intensity and detector sensitivity, for example. The AC detector response is a plethysmograph, as described above. Thus, the red and IR ratios can be denoted as $NP_{RD}$ and $NP_{IR}$ respectively, where NP stands for "normalized plethysmograph." In pulse oximetry, oxygen saturation is calculated from the ratio $NP_{RD}/NP_{IR}$.

SUMMARY OF THE INVENTION

A multiple wavelength sensor and a noninvasive multi-parameter patient monitor, such as referenced above, make blood absorption measurements at more than a red wavelength and an IR wavelength. In one embodiment, described below, blood absorption measurements are made at eight wavelengths. Advantageously, this rich wavelength data, compared with conventional pulse oximetry, allows a determination of a tissue profile or tissue characterization over a wavelength spectrum.

FIG. 2 illustrates an example of a "tissue profile" 200 for SpO2=97%. For this example, including FIGS. 3-4, below, the sensor emits eight wavelengths (610, 620, 630, 655, 700, 720, 800 and 905 nm). The graph is a plot of NP ratios 210 versus wavelength 220, where the NP ratios are of the form $NP_{\lambda 1}/NP_{\lambda 2}$. This is a generalization to multiple wavelengths of the ratio $NP_{RD}/NP_{IR}$ described above for two (red and IR) wavelengths. In order to provide a common scale for these NP ratios, the ratios are calculated with respect to a reference wavelength, $\lambda r$, which may be any of the available wavelengths. Thus, the plotted NP ratios are denoted $NP_{\lambda,i}/NP_{\lambda,r}$ over the n available wavelengths, including $\lambda r$. Note that the NP ratio at the reference wavelength is $NP_{\lambda,r}/NP_{\lambda,r}=1$, which is 800 nm in FIG. 2.

As shown in FIG. 2, when a sensor is properly positioned on a tissue site, the detector only receives LED emitted light that has propagated through the tissue site after tissue scattering and absorption. Thus, a tissue profile 200 should reflect the blood constituent absorption characteristics illustrated in FIG. 1, above. For this high oxygen saturation (97%) example, $HbO_2$ is the only significantly absorbing blood constituent and, indeed, the resulting tissue profile 200 is shaped like the $HbO_2$ absorption curve 110 (FIG. 1).

DETAILED DESCRIPTION OF THE PREFERRED EMBODIMENTS

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 3:
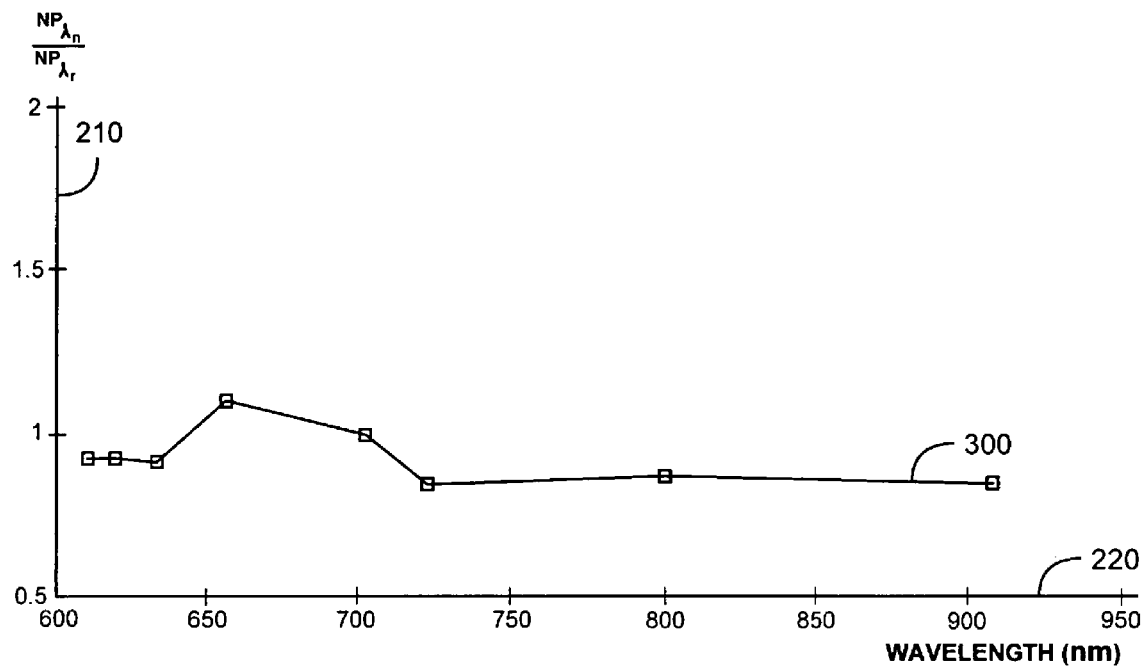
FIG. 3 is a graph of NP ratios versus wavelength illustrating a probe-off profile.

FIG. 3 illustrates an example of a probe-off profile 300. When a sensor is completely dislodged from a patient, a so-called "probe off" condition occurs. Despite a probe off condition, an optical sensor may continue to detect an AC signal, which can be induced at the detector by other than pulsatile arterial absorption of LED emitted light. For example, small patient movements, vibrations, air flow or other perturbations may cause the pathlength between the LEDs and the detector to vary, resulting in an AC detector signal that can be mistakenly interpreted by the monitor as due to pulsatile arterial blood. Further, ambient light may reach the detector, and any modulation of the ambient light due to AC power, power fluctuations, moving objects, such as a fan, among other perturbations can be also mistaken as a pulsatile arterial signal. Probe off errors are serious because a blood constituent monitor may display normal results, such as oxygen saturation, when, in fact, the sensor is not properly attached to the patient, potentially leading to missed severe desaturation events. As shown in FIG. 3, a probe-off profile 300 is readily apparent as it does not have a shape related to the absorption characteristics of hemoglobin constituents.

Figure 1:
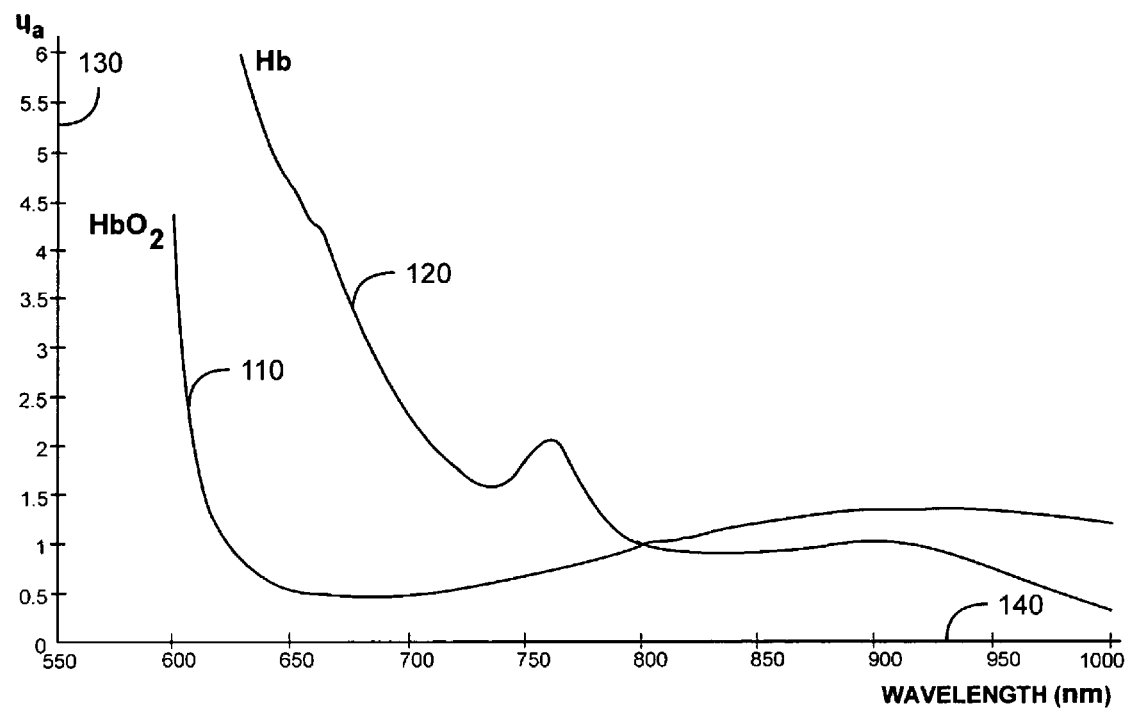
FIG. 1 is a graph of oxyhemoglobin and reduced hemoglobin light absorption versus wavelength across portions of the red and IR spectrum.
Figure 2:
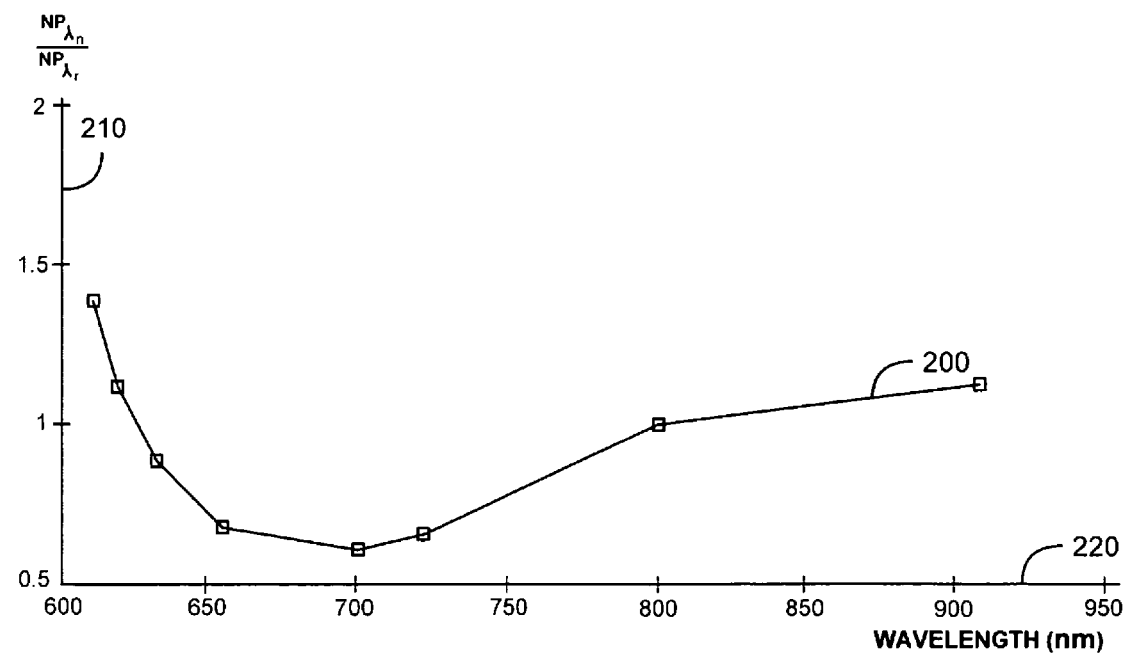
FIG. 2 is a graph of NP ratios versus wavelength illustrating a tissue profile.
Figure 4:
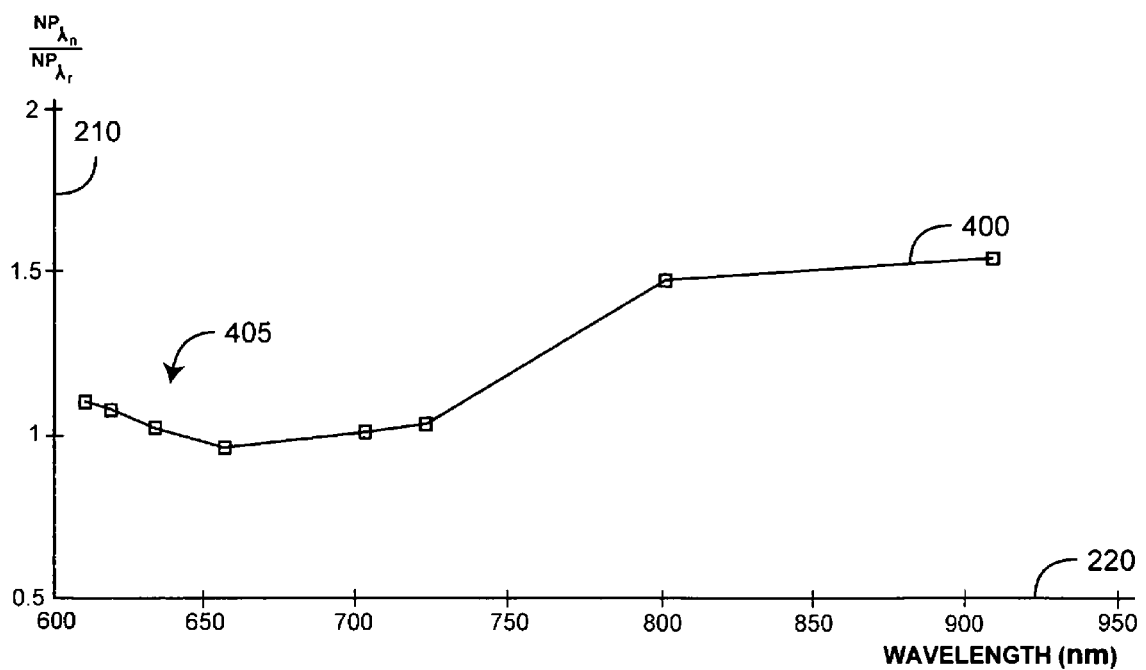
FIG. 4 is a graph of NP ratios versus wavelength illustrating a penumbra profile.

FIG. 4 illustrates an example of a penumbra profile 400. When a sensor is not properly positioned or becomes partially dislodged, a penumbra condition may occur, where the detector is "shadowed" by a tissue site, such as a finger, but also receives some light directly from the emitters or indirectly reflected off the sensor housing, or both. As a result, the DC signal at the detector rises significantly, which lowers the AC/DC ratio (NP). Because red wavelengths are more significantly absorbed by Hb and HbO2, the penumbra condition is most noticeable at the red portion 405 of the $NP_{\lambda,i}/NP_{\lambda,r}$. This effect is readily seen in the penumbra profile 400 as compared to a normal tissue profile 200 (FIG. 2).

Advantageously, a physiological parameter confidence measurement system, as described below, can distinguish a tissue profile 200 (FIG. 2) from a probe-off profile 300 (FIG. 3) or penumbra profile 400 (FIG. 4), as examples. Further, a physiological parameter confidence measurement system can provide indications that the detector signal is degraded as the result of various physiological and non-physiological phenomenon.

Figure 5:
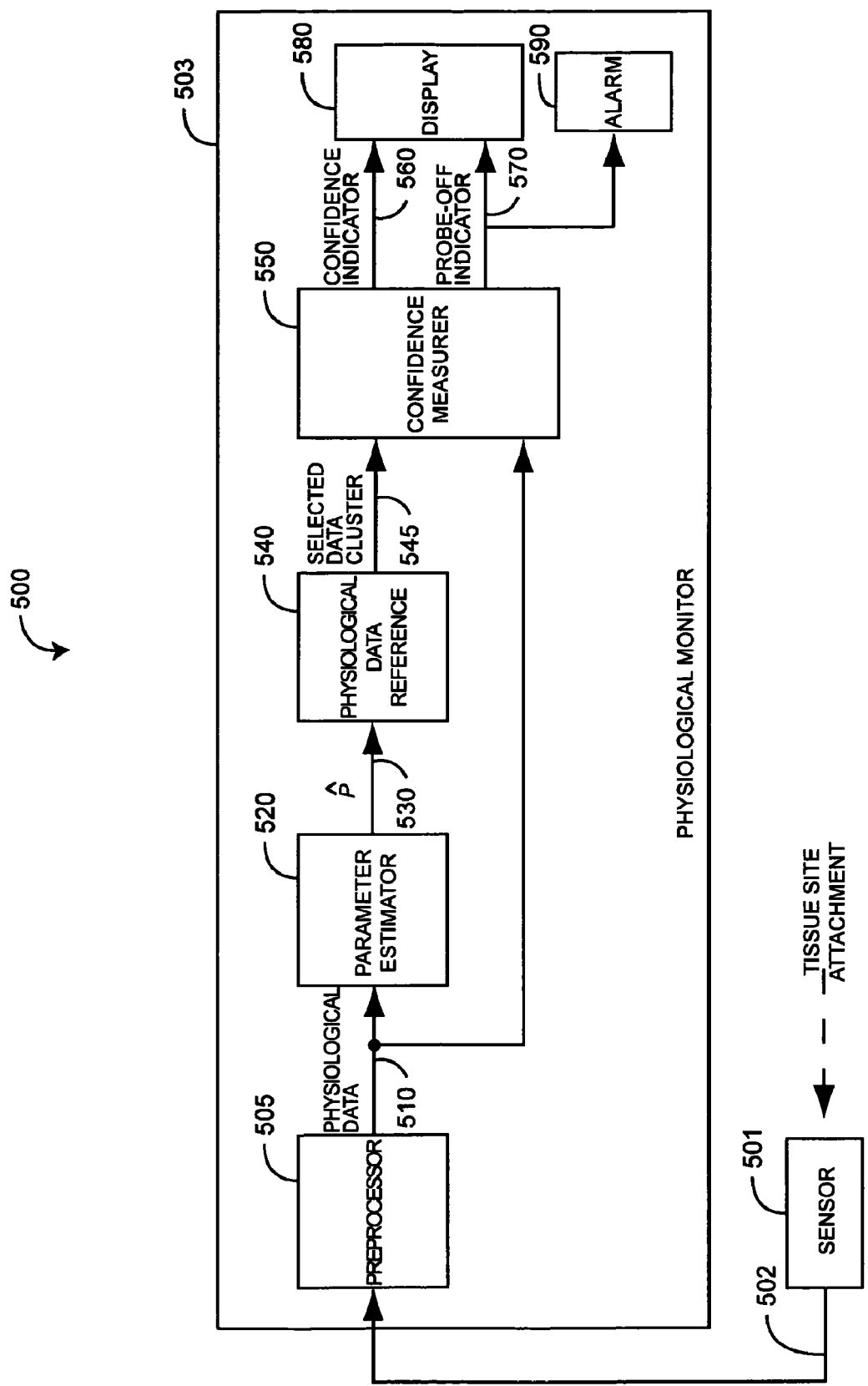
FIG. 5 is a general block diagram of a confidence measurement system.

FIG. 5 illustrates a physiological parameter confidence measurement system 500 having a physiological data 510 input, a confidence indicator 560 output and a probe-off indicator 570 output. In one embodiment, physiological data 510, such as the NP ratios described above, is derived from a sensor 501 generating a sensor signal 502 responsive to multiple wavelengths of optical radiation transmitted into and attenuated by a tissue site. The confidence indicator 560 provides an observer with some measure of "goodness" for the physiological data 510. That is, if confidence is high, it is likely the physiological data 510 is representative of a physiological condition or state. If confidence is low, the physiological data 510 may be less representative of a physiological condition or state. If the confidence is very low, a probe-off indicator 570 may be generated to alert an observer to the possibility that a sensor from which the physiological data 510 is derived is not properly positioned on a tissue site and may not be generating physiologically significant data. In one embodiment, a confidence measure may be provided as a percentage, such as 0-100%. In various embodiments, a confidence indicator 560 corresponding to a confidence measure may be visual or audible or both. For example, a confidence indicator 560 may be a number display, a display message, a bar display, a color indicator or display, such as green (high confidence), yellow (average confidence), red (low confidence). Also, a confidence indicator 560 may be any of various alarm sounds, tones or patterns of sounds or tones, such as a double beep at less than high confidence. In one embodiment, the physiological parameter confidence measurement system 500 is incorporated within a physiological monitor 503 having a display 580 or alarm 590 for outputting the confidence indicator 560 or probe-off indicator 570.

As shown in FIG. 5, the physiological parameter confidence measurement system 500 also has a parameter estimator 520, a physiological data reference 540 and a confidence measurer 550. The parameter estimator 520 derives one or more physiological parameter estimates, P, 530 based upon the physiological data 510. The parameter estimate or estimates 530 are used to select one or more data clusters 545 from the physiological data reference 540. In one embodiment, the physiological data reference 540 is a collection of predetermined physiological data organized in data clusters. For example the physiological data reference 540 may contain clinically-derived physiological data organized according to corresponding values of a physiological parameter determined by a "gold standard" instrument. In a particular embodiment, the physiological data are NP ratios obtained for various physiological parameters, such as $SpO_2$, HbCO, HbMet, Hbt, fractional oxygen saturation, bilirubin or glucose to name a few, as measured with a standardized cooximeter, for example. In one embodiment, the physiological data reference 540 is a non-volatile memory or other data storage device containing predetermined physiological data. The confidence measurer 550 uses the physiological data 510 and the selected data cluster or data clusters 545 to generate the confidence indicator 560, the probe-off indicator 570 or both.

A confidence measurement and confidence indicator, as described herein, may be combined with other signal quality and data confidence measurements and indicators, such as those described in U.S. Pat. No. 6,996,427 titled Pulse Oximetry Data Confidence Indicator and U.S. Pat. No. 6,606,511 titled Pulse Oximetry Pulse Indicator, both patents assigned to Masimo Corporation, Irvine, Calif. and incorporated by reference herein. A probe off measurement and probe off indicator as described herein may be combined with other probe off measurements and indicators, such as those described in U.S. Pat. No. 6,654,624 titled Pulse Oximeter Probe-Off Detector and U.S. Pat. No. 6,771,994 titled Pulse Oximeter Probe-Off Detection System, both patents assigned to Masimo Corporation, Irvine, Calif. and incorporated by reference herein.

Figure 6:
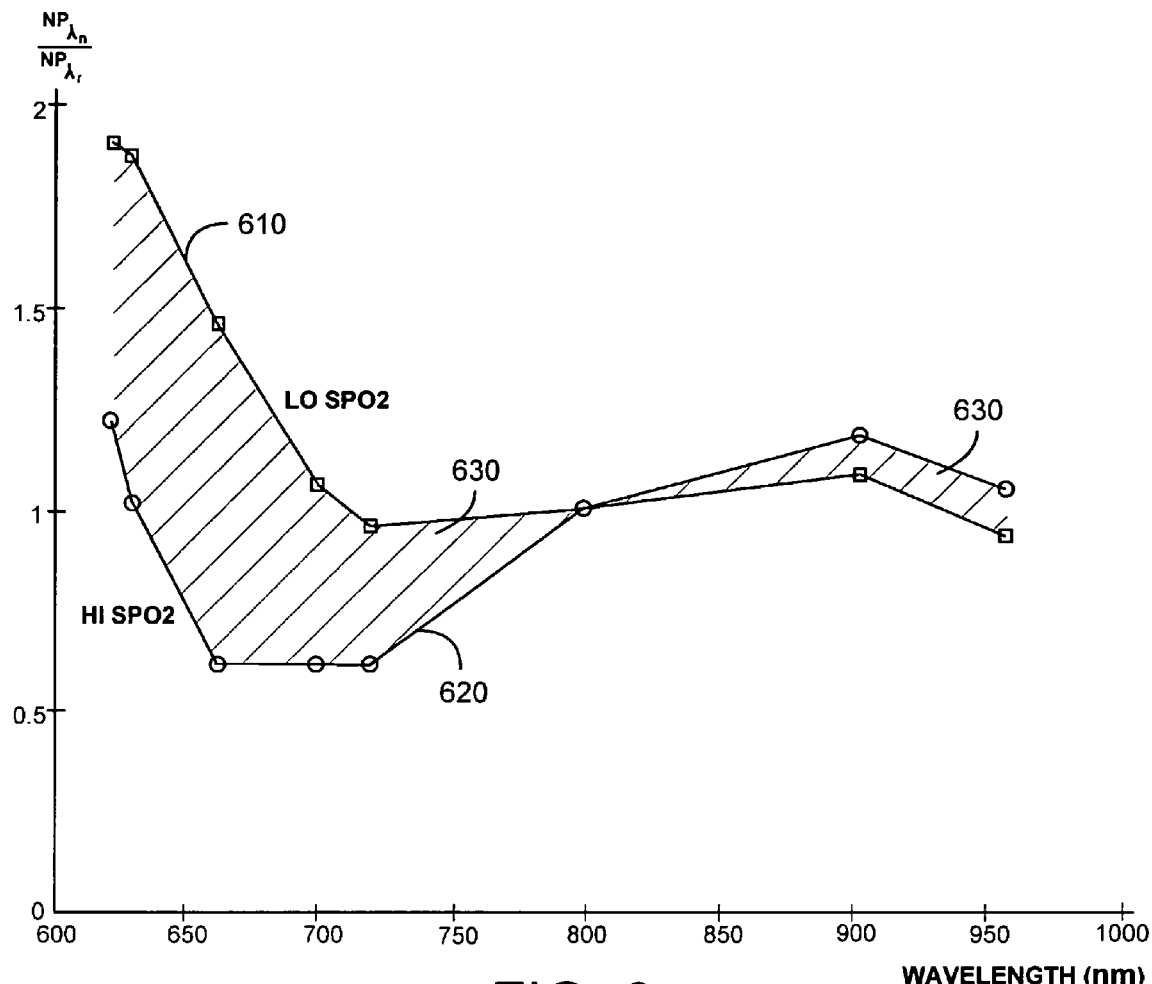
FIG. 6 is a graph of normalized plethysmograph (NP) ratios versus wavelength for low and high $SpO_2$ illustrating a NP envelope.

FIG. 6 illustrates NP ratio versus wavelength curves computed from a multiple wavelength sensor, such as described in the U.S. Patent Application titled Multiple Wavelength Sensor, referenced above. In this example, the sensor emits eight wavelengths (620, 630, 660, 700, 730, 805, 905 and 960 nm). Shown is a low oxygen saturation curve 610, e.g. $SpO_2$=70% and a high oxygen saturation curve 620, e.g. $SpO_2 \approx 100\%$. By comparison, a conventional two wavelength pulse oximetry sensor, as described above, results in a single point on a particular curve. Advantageously, the NP ratio curves 610, 620 represent a tissue profile that can be compared to a particular sensor response to determine if a physiologically significant measurement has been made. In one embodiment, the NP ratio curves 610, 620 delineate the boundaries of a physiologically significant NP ratio region 630. Although described above with respect to $SpO_2$, such regions or boundaries can be derived for other physiological parameters such as HbCO, HbMet, Hbt, fractional oxygen saturation, bilirubin or glucose to name a few.

Figure 7:
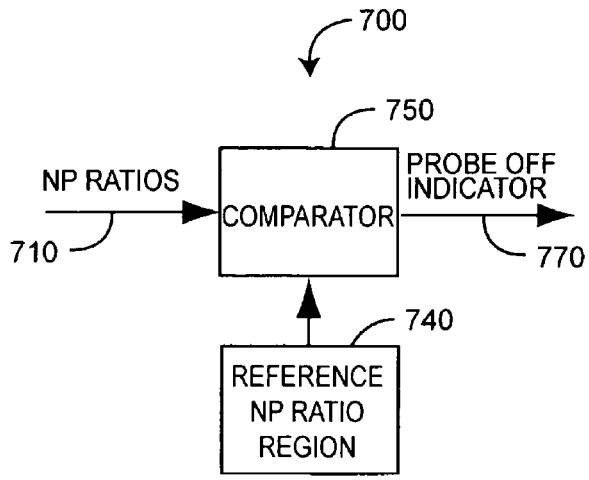
FIG. 7 is a block diagram of a multiple wavelength probe off detector utilizing an NP envelope.

FIG. 7 illustrates one embodiment of a physiological parameter confidence measurement system 700 utilizing a NP ratio region such as described with respect to FIG. 6, above. The confidence measurement system 700 has input NP ratios 710 measured in response to a multiple wavelength sensor, reference NP ratio region 740 that delineates physiologically significant NP ratios 630 (FIG. 6), and a comparator 750. In one particular embodiment, the NP ratio region 740 is predetermined from clinically-derived data for one or more parameters of interest, such as $SpO_2$, HbCO, HbMet, Hbt, fractional oxygen saturation, bilirubin or glucose, to name a few. In another particular embodiment, the NP ratio region 740 is theoretically calculated. The comparator 750 compares the input NP ratios 710 with the NP ratio region 740 and generates a probe-off indicator 770 if any, or more than a predetermine number, of the input NP ratios 710 fall outside of an NP ratio region 740.

Figure 8:
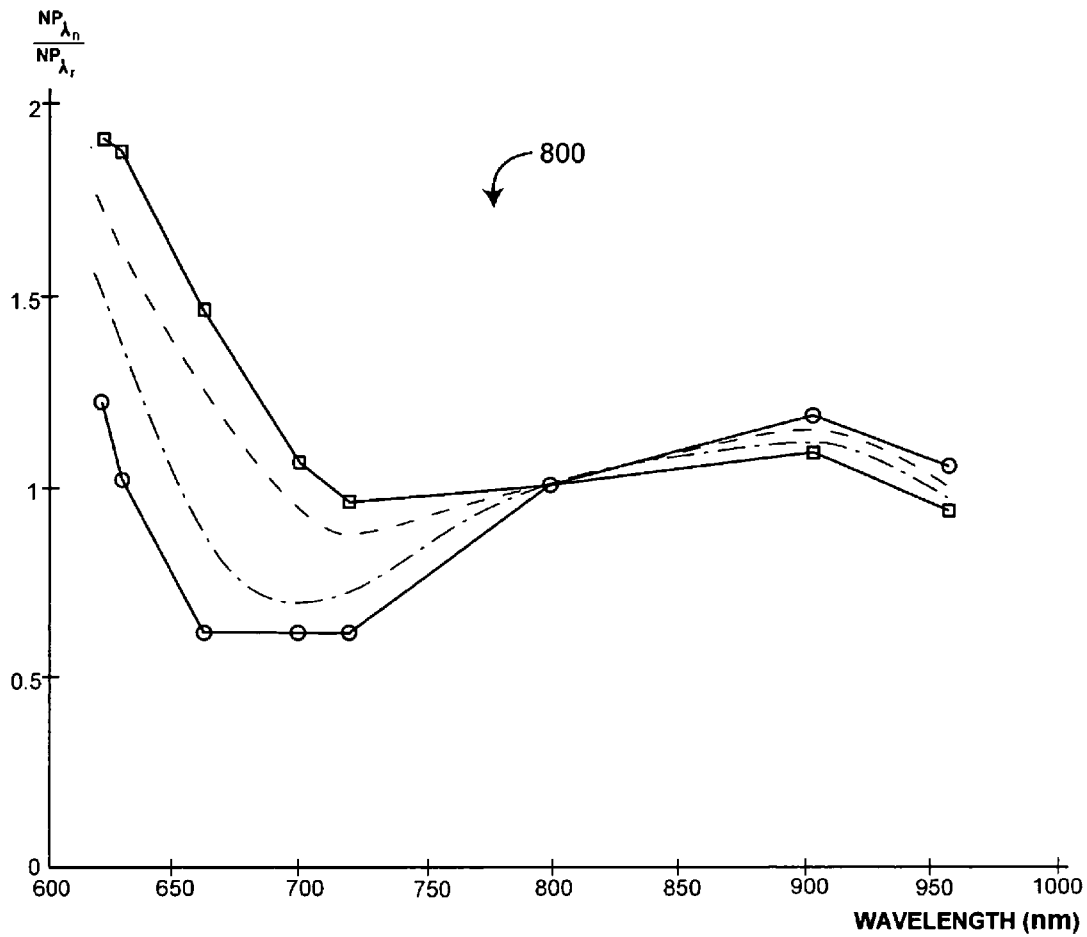
FIG. 8 is a graph of NP ratios versus wavelength illustrating a family of parametric NP curves.

FIG. 8 illustrates a family of parametric NP ratio versus wavelength curves 800 computed from a multiple wavelength sensor, such as referenced above. Each curve represents a different value of a measured parameter, such as $SpO_2$. For example, there may be a curve for each of $SpO_2$=70%, 75%, 80%, . . . 100%. Advantageously, such curves more precisely indicate physiologically significant multiple wavelength sensor measurements as compared to a bounded NP ratio region 630 (FIG. 6) such as described with respect to FIGS. 6-7, above.

Figure 9:
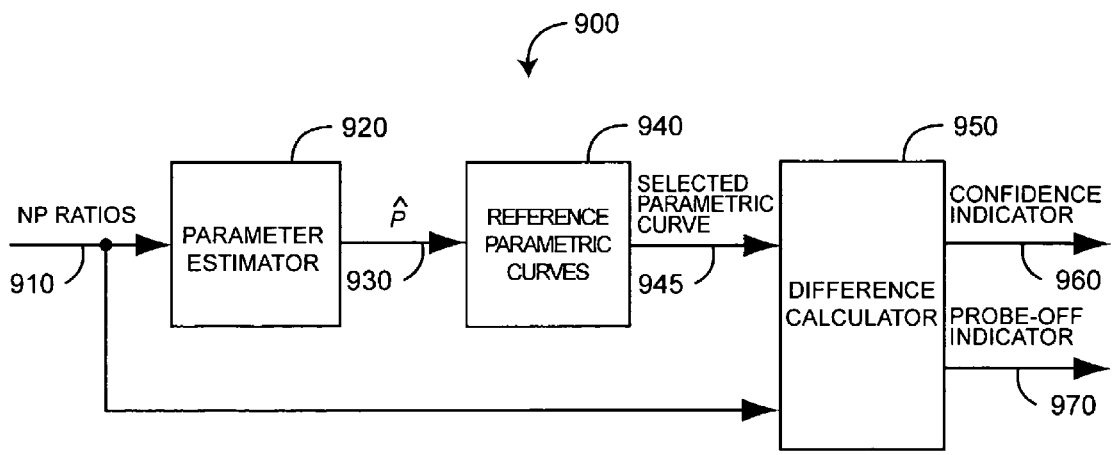
FIG. 9 is a block diagram of a multiple wavelength confidence measurement system utilizing parametric NP curves.

FIG. 9 illustrates another embodiment of a physiological parameter confidence measurement system 900 utilizing parametric NP ratio curves, such as described with respect to FIG. 8, above. The confidence measurement system 900 has input NP ratios 910 measured in response to a multiple wavelength sensor, a parameter estimator 920, reference parametric curves 940 and a difference calculator 950. The parameter estimator 920 inputs the NP ratios 910 so as to generate a parameter estimate 930, such as $SpO_2$, HbCO, HbMet, Hbt, fractional oxygen saturation, bilirubin or glucose, to name a few. The estimated parameter 930 selects one or more of the reference parametric curves 940, which are predetermined from clinically-derived data that is stored in memory or data that is mathematically pre-calculated or calculated in real time and stored in memory. The difference calculator 950 measures the difference between the NP ratios 910 and the selected parametric curve 940. For example, a mean-squared error calculation can be made between the input NP ratios 910 and the selected parametric curve 945. The resulting difference calculation is used as a confidence measure or translated into a confidence measure and a confidence indicator output 960 is generated accordingly. Alternatively, or in addition to a confidence measure, a probe off condition can be indicated if the difference calculation is larger than a predetermined value or the confidence measure is less than a predetermined value. In another embodiment, a correlation calculator is used in place of the difference calculation.

Figure 10:
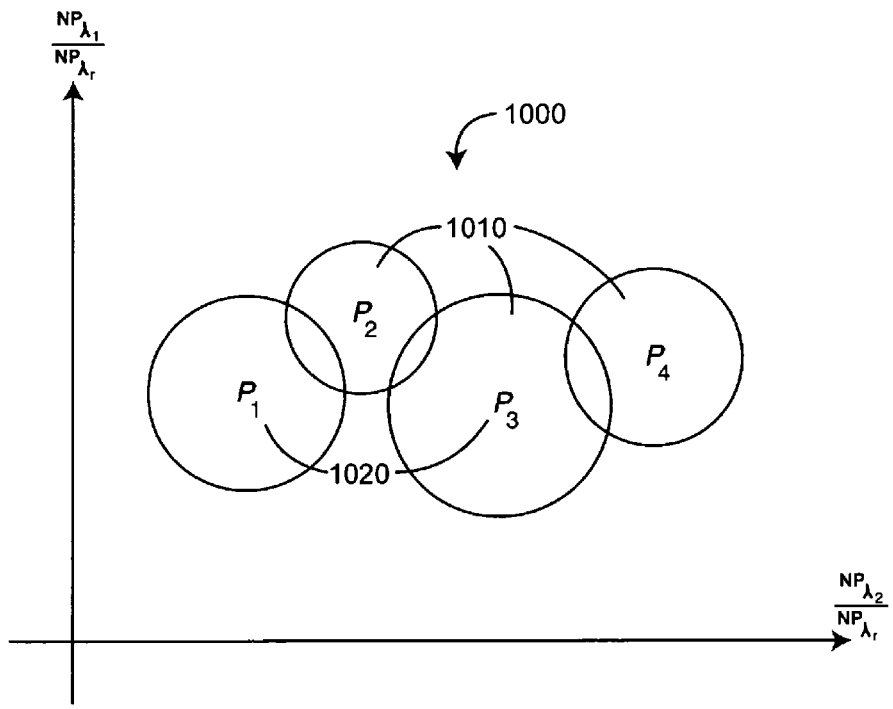
FIG. 10 is an NP ratio graph illustrating a family of NP data clusters.

FIG. 10 illustrates a family of data clusters 1000 shown in two dimensions by way of example. Each data cluster 1000 represents NP ratios clinically measured across a population for specific values 1020 of a selected parameter P, such as $P_1$, $P_2$, $P_3$ and $P_4$ as shown. Each data cluster 1000 defines a region 1010 of NP ratios measured for a particular parameter value 1020 and has a probability distribution, such as a normal distribution, over the indicated region 1010.

For example, the clinical data can be organized as a table of known values of P, corresponding NP ratios measured over a population, and the relative number of occurrences of particular NP ratio values for each value of P. The relative number of occurrences of particular NP ratio values for a particular value of P yields an NP ratio probability distribution for that value of P. Thus, each P value 1020 in the table has a corresponding data cluster 1000 of measured NP ratios and an associated probability distribution for those NP ratios.

Figure 11:
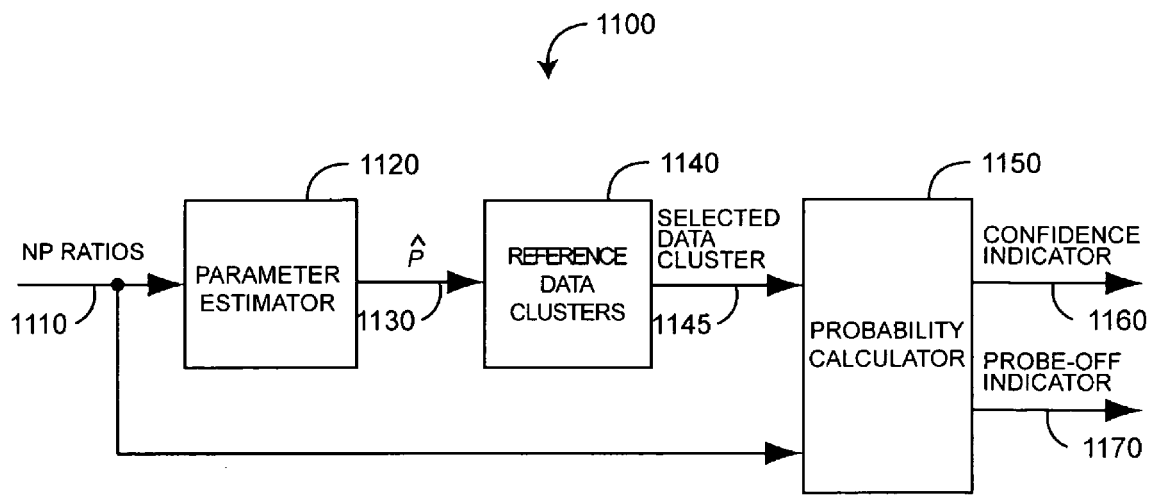
FIG. 11 is a block diagram of a multiple wavelength confidence measurement system utilizing NP data clusters.

FIG. 11 illustrates yet another embodiment of a physiological parameter confidence measurement system 1100 utilizing NP data clusters and corresponding probability distributions, such as described with respect to FIG. 10, above. The confidence measurement system 1100 has input NP ratios 1110 measured in response to a multiple wavelength sensor, a parameter estimator 1120, reference data clusters 1140 and a probability calculator 1150. The parameter estimator 1120 inputs the NP ratios 1110 so as to generate a parameter estimate 1130, such as described with respect to other embodiments, above. In one embodiment, the reference data clusters 1140, such as described with respect to FIG. 10, are stored in a memory device, such as an EPROM. The estimated parameter 1130 is compared with the reference data clusters 1140 so as to determine the closest region 1010 (FIG. 10) or closest overlapping portion of two regions 1010 (FIG. 10). The probability calculator 1150 computes a probability based upon the distribution above the selected region 1010 (FIG. 10). A confidence measure is also derived based upon the calculated probability 1150. In a particular embodiment, the confidence measure is the calculated probability. A confidence indicator 1160 is generated in response to the confidence measure. In one embodiment, if the confidence probability or the calculated confidence measure is below a predetermined threshold, a probe-off indicator 1170 is generated. In particular embodiments, the confidence indicator 1160 or probe-off indicator 1170 or both may be alphanumeric or digital displays, optical indicators or alarms or similar audible indicators, to name a few.

A physiological parameter confidence measurement system has been disclosed in detail in connection with various embodiments. These embodiments are disclosed by way of examples only and are not to limit the scope of the claims that follow. One of ordinary skill in art will appreciate many variations and modifications.

What is claimed is:

1. A method of determining a measure of confidence in a physiological parameter, the physiological parameter determined by transmitting multiple wavelengths of optical radiation into a tissue site and detecting the optical radiation after tissue attenuation, the method comprising:
   deriving physiological data responsive to the intensity of multiple wavelengths of optical radiation transmitted into a tissue site and detected after tissue attenuation;
   estimating a physiological parameter based upon the physiological data;
   providing a physiological data reference;
   obtaining at least one data cluster from the physiological data reference wherein the at least one data cluster is a probability distribution of normalized pleth ratios; and
   determining a measure of confidence in the estimated physiological parameter based upon the at least one data cluster and the derived physiological data.

2. The method according to claim 1 wherein the providing step comprises:
   predetermining the physiological data for known values of the physiological parameter across a sample population;
   clustering the data according to the physiological parameter values; and
   storing the data clusters so as to be retrievable according to the physiological parameter values.

3. The method according to claim 2 wherein the obtaining step comprises selecting the at least one data cluster according to the estimated physiological parameter.

4. The method according to claim 3 wherein the selecting step comprises:
   determining at least one data cluster having a corresponding physiological parameter value closest to the estimated physiological parameter; and
   reading the determined at least one data cluster from the memory.

5. The method according to claim 4 wherein the physiological parameter is at least one of $SpO_2$, MetHb and HbCO.

6. A physiological parameter confidence measurement method comprising:
   deriving physiological data responsive to the intensity of multiple wavelengths of optical radiation transmitted into a tissue site and detected after tissue attenuation;
   estimating a physiological parameter based upon the physiological data;
   providing a physiological data reference having a plurality of data clusters each corresponding to a particular value of the physiological parameter,;
   comparing at least one of the data clusters to the physiological data;
   indicating confidence in the estimated physiological parameter based upon the comparison; and
   associating a probability function with each of the data clusters.

7. The physiological parameter confidence measurement method according to claim 6 wherein the comparing step comprises determining a probability that the derived physiological data corresponds to the estimated physiological parameter.

8. The physiological parameter confidence measurement method according to claim 7 wherein the indicating step comprises generating at least one of a visual indication and an audible indication corresponding to the determined probability.

9. The physiological parameter confidence measurement method according to claim 8 further comprising triggering an alarm that a probe-off condition exists when the determined probability is below a predetermined threshold.

* * * * *